United States Patent [19]

Kukolja et al.

[11] 3,932,387
[45] Jan. 13, 1976

[54] PROCESS FOR THE CONVERSION OF 3-METHYL-3-HYDROXYCEPHAM COMPOUNDS

[75] Inventors: Stjepan P. Kukolja, Indianapolis; Steven R. Lammert, Greenwood, both of Ind.

[73] Assignee: Eli Lilly and Company, Indianapolis, Ind.

[22] Filed: Mar. 27, 1974

[21] Appl. No.: 455,444

Related U.S. Application Data

[63] Continuation-in-part of Ser. No. 267,796, June 30, 1972, abandoned.

[52] U.S. Cl............ 260/239.1; 260/243 C; 424/246; 424/271
[51] Int. Cl.²...................................... C07D 501/04

[58] Field of Search...................... 260/243 C, 239.1

[56] References Cited
UNITED STATES PATENTS
3,852,282  12/1974  Dolfini............................ 260/243 C

*Primary Examiner*—Nicholas S. Rizz
*Assistant Examiner*—Jose Tovar
*Attorney, Agent, or Firm*—William C. Martens, Jr.; Everet F. Smith

[57] ABSTRACT

A 7-imido-3-methyl-3-hydroxycepham-4-carboxylic acid ester is reacted with a halogen reagent in the presence of an alkaline reagent to produce 2-halomethylpenams and a 3-methyl-3-cephem compound.

14 Claims, No Drawings

PROCESS FOR THE CONVERSION OF 3-METHYL-3-HYDROXYCEPHAM COMPOUNDS

CROSS-REFERENCE

This application is a continuation-in-part of application Ser. No. 267,796, filed June 30, 1972, now abandoned.

BACKGROUND OF THE INVENTION

The cephalosporin antibiotics have recently achieved considerable success as therapeutic agents for the treatment of infectious diseases of man. This class of antibiotics is produced by two known general methods. In the first of these methods, cephalosporin C is produced by culturing the organism Cephalosporium acremonium, Newton and Abraham, Biochem. J., 62, 651 (1956). Cleavage of the α-aminoadipoyl side chain of cephalosporin C according to the method described in U.S. Pat. No. 3,188,311 affords 7-aminocephalosporanic acid (7-ACA). Acylation of 7-ACA with an appropriate acyl halide, as, for example, thiophene-2-acetyl chloride, yields the expected 7-acylamidocephalosporanic acid antibiotic. The cephalosporin antibiotics obtained from cephalosporin C according to this method are derivatives of cephalosporanic acid which possesses an acetoxymethyl group attached at the 3-position of the cephalosporin nucleus. According to the cephem nomenclature system for the cephalosporins, the cephalosporin antibiotics obtained from cephalosporin C are named 7-acylamido-3-acetoxymethyl-3-cephem-4-carboxylic acids.

The second method by which the cephalosporin antibiotics are produced involves the chemical conversion of a penicillin antibiotic. This method, described in U.S. Pat. No. 3,275,626, involves the conversion of the thiazolidine ring of a penicillin into the dihydrothiazine ring of a cephalosporin. The fused β-lactam ring of the penicillin molecule remains intact during the conversion. This chemical conversion is carried out by heating a penicillin sulfoxide in the presence of an acidic reagent, such as acetic anhydride, to obtain predominantly a 7-acylamido-3-methyl-3-cephem-4-carboxylic acid ester (a desacetoxycephalosporanic acid) and a 7-acylamido-3-methyl-3-acyloxycepham-4-carboxylic acid ester. Also produced in the chemical conversion process is a 2-acyloxymethylpenicillin, otherwise designated as a 6-acylamido-2-methyl-2-acyloxymethylpenam-3-carboxylic acid.

U.S. Pat. No. 3,275,626 additionally discusses the possibility of converting a penicillin sulfoxide by heating it in the presence of any of various acidic reagents. The ultimate antibiotic substances which form from such reactions will depend to some extent upon the particular acid which is employed, with the substituents present in the acid as well as the particular structure and relative strength of the acid having some effect upon the products formed.

In carrying out the reaction of a penicillin sulfoxide ester with thionyl chloride, it has been found that the following products are obtained:

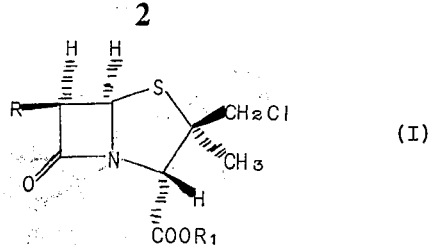

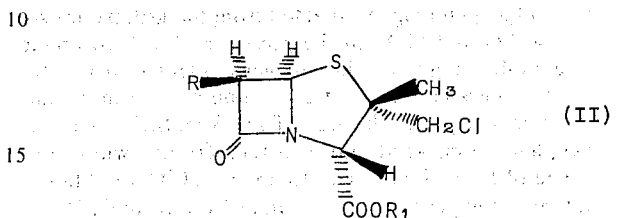

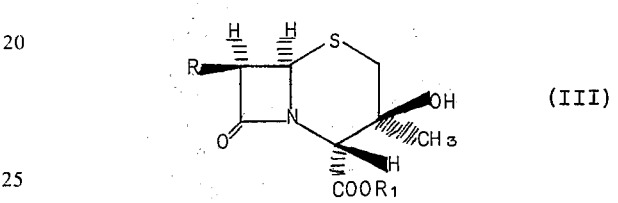

It further has been found that the 2β-chloromethyl-2α-methylpenam (I above) is unstable and gradually rearranges to the corresponding 3α-methyl-3β-chlorocepham of the formula

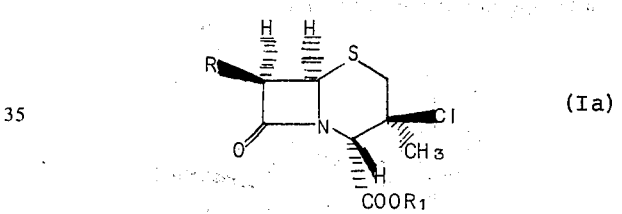

This rearrangement occurs at room temperature over a period of several days. The rearrangement can be greatly accelerated by subjecting the penam to an elevated temperature, for example, from about 50°C. to about 100°C., under which conditions the rearrangement can be accomplished in as little as 1 hour. Conversion to the corresponding 3α-methyl-3β-chlorocepham can also be effected by maintaining the unstable penam in a suitable inert solvent on a chromatographic column for a period of from about 24 to about 72 hours and then eluting the cepham product from the column.

In accordance with this invention, it has now been discovered that it is possible to convert a 7-imido-3β-hydroxycepham-3α-methyl-4-carboxylic acid ester having a structure such as (III) above to an active 3-methyl-3-cephem antibiotic, and, by ring-contraction, to a 2α-halomethylpenam-2β-methyl (penicillin) ring structure and a 2β-halomethylpenam-2α-methyl (penicillin) ring structure.

SUMMARY OF THE INVENTION

The present invention is directed to a process for converting a 3-methyl-3-hydroxycepham compound, which comprises reacting a compound having the formula

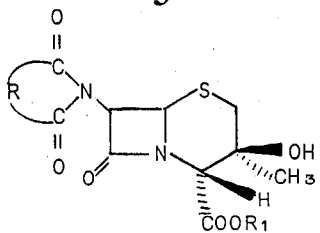

with a halogen reagent selected from the group consisting of PX$_5$ and SOX$_2$ in the presence of at least about one mole of an alkaline reagent selected from the group consisting of a tertiary amine and an inorganic alkaline salt per each mole of the 3-methyl-3-hydroxycepham compound and at a temperature within the range of from about 60°C. to about 150°C. to obtain a mixture comprising a compound of the formula IV

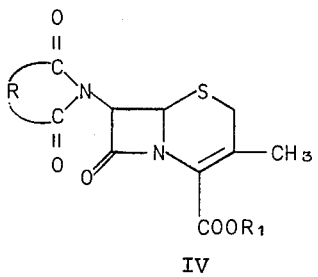

IV a compound of the formula V

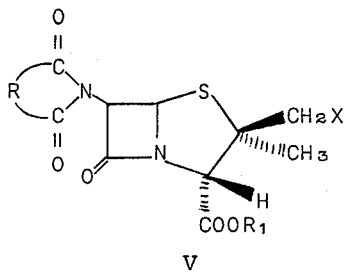

V and a compound of the formula VI

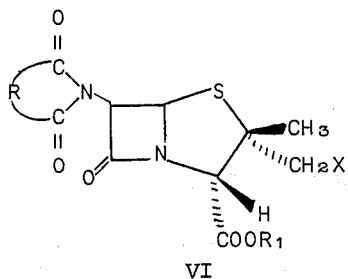

VI in which, in the above formulae, R is the residue of an imide derived from a dicarboxylic acid, R$_1$ is a carboxy protecting group and X is chlorine or bromine.

As stated hereinabove, the 2β-chloromethylpenam-2α-methyl structure rearranges over a period of time to the corresponding 3α-methyl-3β-chlorocepham. This is likewise true of the 2β-halomethylpenam-2α-methyl structure (V) whether X therein is chlorine or bromine. Indeed, in those instances in which X is bromine, the rearrangement of the 2β-halomethylpenam-2α-methyl structure to the 3α-methyl-3β-halocepham (Va)

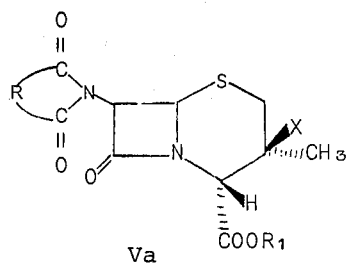

Va is substantially more rapid than in those instances in which X is chlorine. Virtually complete rearrangement will be accomplished merely by allowing the 2β-bromomethylpenam-2α-methyl compound to stand at room temperature for a period of from about 24 to about 72 hours.

DETAILED DESCRIPTION OF THE INVENTION

The process of this invention is carried out by heating a 7-imido-3α-methyl-3β-hydroxycepham-4-carboxylic acid ester in the presence of a halogen reagent selected from the group consisting of phosphorus pentachloride, thionyl chloride, phosphorus pentabromide, and thionyl bromide, and in the presence of an alkaline reagent.

The reaction is carried out at a temperature within the range of from about 60°C. to about 150°C. More preferably, the temperature of reaction is between 75°C. and 100°C. Typically, the time of reaction will range from about 30 minutes to about 2 hours, with the reaction time to some degree being dependent upon the particular reactants which are employed as well as the temperature at which the reaction is carried out. Normally, the higher the temperature of reaction the shorter the reaction time. Usually, the reaction will be completed after the reactants have been maintained in contact at the selected reaction temperature for about 30 to about 45 minutes.

Also, it is pointed out that, depending upon the time and temperature of reaction, it is possible to recover from the reaction mixture amounts of the 3α-methyl-3β-halocepham. The immediate precursor of this structure, nevertheless, is the 2β-halomethylpenam-2α-methyl compound produced by the process of this invention.

The conversion of the 3-methyl-3-hydroxycepham compound preferably is carried out in the presence of a suitable inert solvent, specifically, one which will facilitate adequate mixing of the reactants. Suitable solvents are those having a boiling point at least as high as the temperature of reaction and include, for example, aromatic hydrocarbons such as benzene and toluene; halogenated hydrocarbons such as carbon tetrachloride, chlorobenzene, bromoform, bromobenzene, 1,2-dichloroethane, 1,2-dibromoethane, and the like; amides, such as N,N-dimethylformamide, N,N-dimethylacetamide, and the like; aliphatic nitriles, such as acetonitrile, propionitrile, and the like; esters, such as ethyl acetate, and the like; ethers, such as dioxane, and the like; and any other appropriate inert solvents. Preferred solvents are those having a boiling point within the temperature range at which the reaction is to be carried out, thereby permitting the reaction mixture to be refluxed while retaining temperature control.

The conversion of the 3-methyl-3-hydroxycepham compound is accomplished in the presence of both the halogen reagent and an alkaline reagent. The halogen reagent is selected from the group consisting of phosphorous pentachloride, thionyl chloride, phosphorous pentabromide, and thionyl bromide. In order to ensure the presence of sufficient halogen reagent, preferably at least one mole of the halogen reagent is used per each mole of the 3-methyl-3-hydroxycepham. Usually a molar excess of the halogen reagent will be employed, and typically the amount of halogen reagent will range from slightly over equimolar to about 2.5 moles of the halogen reagent per mole of the 3-methyl-3-hydroxycepham compound. Preferably, the halogen reagent will be present in an amount of from about 1.1 to about 2.0 moles per each mole of the 3-methyl-3-hydroxycepham compound.

The identity of the halo group present in the 2-halomethylpenam compounds which are formed is dependent upon the identity of the halogen in the halogen reagent. If the halogen reagent is a chlorine compound, the products will be the two isomeric 2-chloromethylpenams, and a 3-methyl-3-cephem. If the halogen reagent is a bromine compound, the products will be the two isomeric 2-bromomethylpenams, and a 3-methyl-3-cephem.

The other reactant which is employed in the conversion of the 3-methyl-3-hydroxycepham is an alkaline reagent. Alkaline reagents which are suitable for conversion of the 3hydroxycepham include tertiary amines and inorganic alkaline salts. Examples of suitable tertiary amines include those which contain alkyl groups having from one to five carbon atoms, such as trimethylamine, triethylamine, tripropylamine, tributylamine, triamylamine, methyldiethylamine, and the like. Other suitable tertiary amines include cyclic amines, such as pyridine, quinoline, N-methylmorpholine, N-methylpiperidine, and the like. Suitable typical inorganic alkaline salts include sodium carbonate, sodium bicarbonate, sodium acetate, potassium carbonate, potassium bicarbonate, potassium acetate, lithium carbonate, lithium bicarbonate, lithium acetate, disodium hydrogen phosphate, trisodium phosphate, dipotassium hydrogen phosphate, tripotassium phosphate, sodium benzoate, potassium benzoate, sodium formate, potassium formate, disodium phthalate, potassium hydrogen phthalate, and the like.

The alkaline reagent which is employed must be present in an amount at least about equimolar to the 3-methyl-3-hydroxycepham compound. The amount of alkaline reagent which is employed has some effect on the relative ratio of the products which will be formed from the conversion. Generally, as the amount of alkaline reagent is increased above one mole per each mole of the 3-methyl-3-hydroxycepham compound, the relative amount of the 7-imido-3-methyl-3-cephem-4-carboxylic acid ester (IV) present in the product mixture will be increased. Preferably, from about 1.0 to about 2.0 moles of the alkaline reagent will be employed per each mole of the 3-methyl-3-hydroxycepham compound, and, more preferably, the molar ratio of alkaline reagent to 3-methyl-3-hydroxycepham will be from about 1.1 to about 1.5.

As mentioned hereinabove, the 3-methyl-3-hydroxycepham compound used as starting material in the process of this invention can be prepared by reacting the corresponding penicillin sulfoxide with thionyl chloride in accordance with the general reaction described in U.S. Pat. No. 3,275,626. The 3-methyl-3-hydroxycepham compounds are also available in accordance with the techniques described in U.S. Pat. Nos. 3,668,201 and 3,668,202. These involve heating a penicillin sulfoxide in the presence of sulfuric or sulfamic acid in a solvent system containing a tertiary carboxamide.

The 3-methyl-3-hydroxycepham used as starting material in the process of this invention has the following formula:

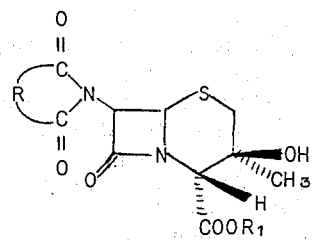

$R_1$ in the above formula as well as in the products of the process of this invention denotes a carboxy protecting group. The nature of the carboxy protecting group is not important, and any of those known in the art can be used. Preferably, however, this group is the residue of an ester function which is removable by acid treatment or by hydrogenation. Preferred carboxy protecting groups include, for example, $C_1$-$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, phenacyl, or p-halophenacyl, in any of the above of which halo denotes chlorine, bromine, or iodine.

Specific illustrations of the preferred ester residues of the carboxyl group of the 3-hydroxycepham compound used in the process of this invention include, for example, methyl, ethyl, n-propyl, isopropyl, n-butyl, secbutyl, isobutyl, t-butyl, 2,2,2-trichloroethyl, 2,2,2-tribromoethyl, 2-iodoethyl, benzyl, p-nitrobenzyl, succinimidomethyl, phthalimidomethyl, p-methoxybenzyl, benzhydryl, acetoxymethyl, pivaloyloxymethyl, propionoxymethyl, phenacyl, p-chlorophenacyl, p-bromophenacyl, and the like.

Highly preferred ester residues are methyl, benzyl, p-nitrobenzyl, p-methoxybenzyl, benzhydryl, and 2,2,2-trichloroethyl.

In the above formula as well as in those depicting the products of the process of this invention, the cyclic imide radical defined by R taken together with the nitrogen-dicarbonyl combination to which it is bonded can be obtained by reacting a precursor of the 3-methyl-3-hydroxycepham compound, such as the 6-amino group of 6-aminopenicillanic acid (6-APA) or an ester of 6-APA with a dicarboxylic acid or anhydride or other reactive variant thereof, and treating the resulting derivative with a $C_1$-$C_4$ alkyl haloformate, for example, ethyl chloroformate, in the presence of an organic base. Preferably, R is $C_2$-$C_4$ alkylene, $C_2$-$C_4$ alkenylene, -$CH_2$-Y-$CH_2$- in which Y is oxygen or sulfur, 1,2-cyclohexylene, 1,2-phenylene, 1,2-cyclohexenylene, or a substituted derivative of any of these having from 1 to 4 substituents selected from the group consisting of $C_1$-$C_3$ alkyl, $C_1$-$C_3$ alkoxy, nitro, fluoro, chloro, bromo and iodo. More preferably, R is $C_2$-$C_4$ alkylene, $C_2$-$C_4$ alkenylene, -$CH_2$-Y-$CH_2$- in which Y is oxygen or sulfur, 1,2-cyclohexylene, 1,2-phenylene, or 1,2-cyclohexenylene, each of which is unsubstituted or singly substituted with any of the aforementioned substitutents. Typically, R is the residue of a $C_4$ to $C_{10}$ dicarboxylic acid, and the cyclic imide thus represented is prepared from such dicarboxylic acid, its anhydride, or an appropriate reactive variant thereof. Cyclic imides can be prepared, for example, from acids such as succinic, maleic, glutaric, diglycolic, thiodiglycolic, phthalic, and the like, or their resoective anhydrides, as well as from cyclohexane-1,2-dicarboxylic, 3-cyclohexene-1,2-dicarboxylic, halogen substituted dicarboxylic acids or anhydrides such as 4,5-dichlorophthalic, tetraiodophthalic, 4-bromophthalic, nitro substituted dicarboxylic acids and anhydrides such as 3-nitrophthalic acid, alkyl substituted dicarboxylic acids and anhydrides such as methylmaleic acid, as well as related compounds and compounds of similar reactivities. Additional examples of cyclic anhydrides of the type defined are found in the prior art such as in the *Journal of Organic Chemistry*, Volume 26, pp. 3,365–3,367 (September, 1961). 6-Phthalimidopenicillanic acid can also be prepared from 6-APA and N-carboethoxyphthalimide according to the procedure of Y. G. Perron et al., *Journal of Medicinal Chemistry*, Volume 5, (1962), p. 1016.

The thus-produced 6-imido-substituted penicillanic acid or ester can then be oxidized in accordance with known techniques to produce the penicillin sulfoxide. This sulfoxide, having an appropriate carboxy protecting group, can then be reacted in accordance with the teaching provided in U.S. Pat. No. 3,275,626 or that provided in U.S. Pat. Nos. 3,668,201 and 3,668,202, to produce the 3-hydroxycepham starting material.

Representative of the product conversions which are available in accordance with the process of this invention are the following. It will be understood, however, that the ratio of products may vary depending upon the particular reactants which are employed, the relative quantities of reactants, and the conditions of reaction.

Methyl 7-phthalimido-3α-methyl-3β-hydroxycepham-4-carboxylate to methyl 7-phthalimido-3-methyl-3-cephem-4-carboxylate, methyl 6-phthalimido-2α-halomethylpenam-2β-methyl-3-carboxylate, and methyl 6-phthalimido-2β-halomethylpenam-2α-methyl-3-carboxylate, the latter rearranging over a period of time to methyl 7-phthalimido-3α-methyl-3β-halocepham-4-carboxylate.

2,2,2-Trichloroethyl 7-phthalimido-3α-methyl-3β-hydroxycepham-4-carboxylate to 2,2,2-trichloroethyl 7-phthalimido-3-methyl-3-cephem-4-carboxylate, 2,2,2-trichloroethyl 6-phthalimido-2α-halomethylpenam-2β-methyl-3-carboxylate, and 2,2,2-trichloroethyl 6-phthalimido-2β-halomethylpenam-2α-methyl-3-carboxylate, the latter rearranging over a period of time to 2,2,2-trichloroethyl 7-phthalimido-3α-methyl-3β-halocepham-4-carboxylate.

p-Nitrobenzyl 7-phthalimido-3α-methyl-3β-hydroxycepham-4-carboxylate to p-nitropbenzyl 7-phthalimido-3-methyl-3-cephem-4-carboxylate, p-nitrobenzyl 6-phthalimido-2α-halomethylpenam-2β-methyl-3-carboxylate, and p-nitrobenzyl 6-phthalimido-2β-halomethylpenam-2α-methyl-3-carboxylate, the latter rearranging over a period of time to p-nitrobenzyl 7-phthalimido-3α-methyl-3β-halocepham-4-carboxylate.

Benzyl 7-succinimido-3α-methyl-3β-hydroxycepham-4-carboxylate to benzyl 7-succinimido-3-methyl-3-cephem-4-carboxylate, benzyl 6-succinimido-2α-halomethylpenam-2β-methyl-3-carboxylate, and benzyl 6-succinimido-2β-halomethylpenam-2α-methyl-3-carboxylate, the latter rearranging over a period of time to benzyl 7-succinimido-3α-methyl-3β-halocepham-4-carboxylate.

Benzhydryl 7-phthalimido-3α-methyl-3β-hydroxycepham-4-carboxylate to benzhydryl 7-phthalimido-3-methyl-3-cephem-4-carboxylate, benzyhydryl 6-phthalimido-2α-halomethylpenam-2β-methyl-3-carboxylate, and benzhydryl 6-phthalimido-2β-halomethylpenam-2α-methyl-3-carboxylate, the latter rearranging over a period of time to benzhydryl 7-phthalimido-3α-methyl-3βhalocepham-4-carboxylate.

t-Butyl 7-glutarimido-3α-methyl-3β-hydroxycepham-4-carboxylate to t-butyl 7-glutarimido-3-methyl-3-cephem-4-carboxylate, t-butyl 6-glutarimido-2α-halomethylpenam-2β-methyl-3-carboxylate, and t-butyl 6-glutarimido-2β-halomethylpenam-2α-methyl-3-carboxylate, the latter rearranging over a period of time to t-butyl 7-glutarimido-3α-methyl-3β-halocepham-4-carboxylate.

p-Nitrobenzyl 7-diglycolimido-3α-methyl-3β-hydroxycepham-4-carboxylate to p-nitrobenzyl 7-diglycolimido-3-methyl-3-cephem-4-carboxylate, p-nitrobenzyl 6-diglycolimido-2α-halomethylpenam-2β-methyl-3-carboxylate, and p-nitropbenzyl 6-diglycolimido-2β-halomethylpenam-2α-methyl-3-carboxylate, the latter rearranging over a period of time to p-nitrobenzyl 7-diglycolimido-3α-methyl-3β-halocepham-4-carboxylate.

Benzhydryl 7-(3'-bromophthalimido)-3α-methyl-3β-hydroxycepham-4-carboxylate to benzhydryl 7-(3'-bromophthalimido)--3-methyl-3-cepham-4-carboxylate, benzhydryl 6-(3'-bromophthalimido)-2α-halomethylpenam-2β-methyl-3-carboxylate, and benzhydryl 6-(3'-bromophthalimido)-2β-halomethylpenam-2α-methyl-3-carboxylate, the latter rearranging over a period of time to benzhydryl 7-(3'-bromophthalimido)-3α-methyl-3β-halocepham-4-carboxylate.

p-Nitrobenzyl 7-tetraiodophthalimido-3α-methyl-3β-hydroxycepham-4-carboxylate to p-nitrobenzyl 7-tetraiodophthalimido-3-methyl-3-cephem-4-carboxylate, p-nitrobenzyl 6-tetraiodophthalimido-2α-halomethylpenam-2β-methyl-3-carboxylate, and p-nitrobenzyl 6-tetraiodophthalimido-2β-halomethylpenam-2α-methyl-3-carboxylate, the latter rearranging over a period of time to p-nitrobenzyl 7-tetraiodophthalimido-3α-methyl-3β-halocepham-4-carboxylate.

p-Methoxybenzyl 7-(3'-nitrophthalimido)-3α-methyl-3β-hydroxycepham-4-carboxylate to p-methoxybenzyl 7-(3'-nitrophthalimido)-3-methyl-3-cephem-4-carboxylate, p-methoxybenzyl 6-(3'-nitrophthalimido)-2α-halomethylpenam-2β-methyl-3-carboxylate, and p-methoxybenzyl 6-(3'-nitrophthalimido)-2β-halomethylpenam-2α-methyl-3-carboxylate, the latter rearranging over a period of time to p-methoxybenzyl 7-(3'-nitrophthalimido)-3α-methyl-3β-halocepham-4-carboxylate.

Phthalimidomethyl 7-(4',5'-dichlorophthalimido)-3α-methyl-3β-hydroxycepham-4-carboxylate to phthalimidomethyl 7-(4',5'-dichlorophthalimido)-3-methyl-3-cephem-4-carboxylate, phthalimidomethyl 6-(4',5'-dichlorophthalimido)-2α-halomethylpenam-2β-methyl-3-carboxylate, and phthalimidomethyl 6-(4',5'-dichlorophthalimido)-2β-halomethylpenam-2α-methyl-3-carboxylate, the latter rearranging over a period of time to phthalimidomethyl 7-(4',5'-dichlorophthalimido)-3α-methyl-3β-halocepham-4-carboxylate.

Succinimidomethyl 7-hexahydrophthalimido-3α-methyl-3β-hydroxycepham-4-carboxylate to succinimidomethyl 7-hexahydrophthalimido-3-methyl-3-cephem-4-carboxylate, succinimidomethyl 6-hexahydrophthalimido-2α-halomethylpenam-2β-methyl-3-carboxylate, and succinimidomethyl 6-hexahydrophthalimido-2β-halomethylpehan-2α-methyl-3-carboxylate, the latter rearranging over a period of time to succinimidomethyl 7-hexahydrophthalimido-3α-methyl-3β-halocepham-4-carboxylate Iodoethyl 7-diglycolimido-3α-methyl-3β-hydroxycepham-4-carboxylate to iodoethyl 7-diglycolimido-3-methyl-3-cephem-4-carboxylate, iodoethyl 6-diglycolimido-2α-halomethylpenam-2β-methyl-3-carboxylate, and iodoethyl 6-diglycolimido-2β-halomethylpenam-2α-methyl-3-carboxylate, the latter rearranging over a period of time to iodoethyl 7-diglycolimido-3α-methyl-3β-halocepham-4-carboxylate.

Pivaloyloxymethyl 7-(1',2',3',6'-tetrahydrophthalimido)-3α-methyl-3β-hydroxycephem-4-carboxylate to pivaloyloxymethyl 7-(1',2',3',6'-tetrahydrophthalimido)-3-methyl-3-cephem-4-carboxylate, pivaloyloxymethyl 6-(1',2',3',6'-tetrahydrophthalimido)-2α-halomethylpenam-2β-methyl-3-carboxylate, and pivaloyloxymethyl 6-(1',2',3',6'-tetrahydrophthalimido)-2β-halomethylphenam-2α-methyl-3-carboxylate, the latter rearranging over a period of time to pivaloyloxymethyl 7-(1',2',3',6'-tetrahydrophthalimido)-3α-methyl-3β-halocepham-4-carboxylate.

Acetoxymethyl 7-(3'-methylphthalimido)-3α-methyl-3β-hydroxycepham-4-carboxylate to acetoxymethyl 7-(3'-methyl-phthalimido)-3-methyl-3-cephem-4-carboxylate, acetoxymethyl 6-(3'-methylphthalimido)-2α-halomethylpenam-2β-methyl-3-carboxylate, and acetoxymethyl 6-(3'-methylphthalimido)-2β-halomethylpenam-2α-methyl-3-carboxylate, the latter rearranging over a period of time to acetoxymethyl 7-(3'-methylphthalimido)-3α-methyl-3β-halocepham-4-carboxylate.

Phenacyl 7-(4'-methoxyphthalimido)-3α-methyl-3β-hydroxycepham-4-carboxylate to phenacyl 7-(4'-methoxyphthalimido)-3-methyl-3-cephem-4-carboxylate, phenacyl 6(4'-methoxyphthalimido)-2α-halomethylpenam-2β-methyl-3-carboxylate, and phenacyl 6-(4'-methoxyphthalimido)-2β-halomethylpenam-2α-methyl-3-carboxylate; the latter rearranging over a period of time to phenacyl 7-(4'-methoxyphthalimido)-3α-methyl-3β-halocepham-4-carobxylate.

p-Nitrobenzyl 7-thiodiglycolimido-3α-methyl-3β-hydroxycepham-4-carboxylate to p-nitrobenzyl 7-thiodiglycolimido-3-methyl-3-cephem-4-carboxylate, p-nitrobenzyl 6-thiodiglycolimido-2α-halomethylpenam-2β-methyl-3-carboxylate, and p-nitrobenzyl 6-thiodiglycalimido-2β-halomethylpenam-2α-methyl-3-carobxylate, the latter rearranging over a period of time to p-nitrobenzyl 7-thiodiglycolimido-3α-methyl-3βhalocepham-4-carboxylate.

p-Chlorophenacyl 7-glutarimido-3α-methyl-3β-hydroxycepham-4-carboxylate to p-chlorophenacyl 7-glutarimido-3-methyl-3-cephem-4-carboxylate, p-chlorophenacyl 6-glutarimido-2α-halomethylpenam-2β-methyl-3-carboxylate, and p-chlorophenacyl 6-glutarimido-2β-halomethylpenam-2α-methyl-3-carboxylate, the latter rearranging over a period of time to p-chlorophenacyl 7-glutarimido-3α-methyl-3β-halocepham-4-carboxylate.

2,2,2-Trichloroethyl 7-(3'-isopropylphthalimido)-3α-methyl-3β-hydroxycepham-4-carboxylate to 2,2,2-trichloroethyl 7-(3'-isopropylphthalimido)-3-methyl-3-cephem-4-carboxylate, 2,2,2-trichloroethyl 6-(3'-isopropylphthalimido)-2α-halomethylpenam-2β-methyl-3-carboxylate, and 2,2,2-trichloroethyl 6-(3'-isopropylphthalimido)-2β-halomethylpenam-2α-methyl-3-carboxylate, the latter rearranging over a period of time to 2,2,2-trichloroethyl 7-(3'-isopropylphthalimido)-3α-methyl-3β-halocepham-4-carboxylate.

p-Methoxybenzyl 7-(3'-fluorophthalimido)-3α-methyl-3β-hydroxycepham-4-carboxylate to p-methoxybenzyl 7-(3'-fluorophthalimido)-3-methyl-3-cephem-4-carboxylate, p-methoxybenzyl 6-(3'-fluorophthalimido)-2α-halomethylpenam-2β-methyl-3-carboxylate, and p-methoxybenzyl 6-(3'-fluorophthalimido)-2β-halomethylpenam-2α-methyl-3-carboxylate, the latter rearranging over a period of time to p-methoxybenzyl 7-(3'-fluorophthalimido)-3α-methyl-3β-halocepham-4-carboxylate.

p-Nitrobenzyl 7-(1',4',5',6'-tetrahydrophthalimido)-3α-methyl-3β-hydroxycepham-4-carboxylate to p-nitrobenzyl 7-(1',4',5',6'-tetrahydrophthalimido)-3-methyl-3-cephem-4-carboxylate, p-nitrobenzyl 6-(1',4',5',6'-tetrahydrophthalimido)-2α-halomethylpenam-2β-methyl-3-carboxylate, and p-nitrobenzyl 6-(1',4',5',6'-tetrahydrophthalimido)-2β-halomethylpenam-2α-methyl-3-carboxylate, the latter rearranging over a period of time to p-nitrobenzyl 7-(1',4',5',6'-tetrahydrophthalimido)-3α-methyl-3β-halocepham-4-carboxylate.

In the above representative conversions, the term "halo" refers to chloro or bromo. Whether the products are the chloro or the bromo derivatives is determined by the identity of the particular halogen compound employed in the reaction.

The products produced in accordance with the process of this invention can be isolated by employing conventional methods. These can include, for example, chromatographic separation, filtration, recrystallization, and the like.

The 3-methyl-3-cephem (desacetoxycephalosporin) ester produced by the process of this invention can be converted by known techniques to an active antibiotic by cleavage of the ester function. Deesterification can be achieved by treatment of the ester with an acid such as trifluoroacetic acid, hydrochloric acid, and the like, or with zinc and acid, such as formic acid, acetic acid, or hydrochloric acid. It can likewise be accomplished by hydrogenating the ester in the presence of palladium, rhodium, or a compound thereof, in suspension or on a carrier such as barium sulfate, carbon, alumina, or the like.

Furthermore, other active antibiotics can be obtained from the previously or subsequently deesterified 3-methyl-3-cephem compound either by opening the 7-imido substituent to form a 7-amido derivative or by cleaving the 7-imido substituent and acylating the resulting 7-aminodesacetoxycephalosporin (7-ADCA).

The following examples are provided to further illustrate this invention. It is not intended that this invention be limited in scope by reason of any of these examples.

EXAMPLE I

Preparation of Methyl 7-Phthalimido-3α-methyl-3β-hydroxycepham-4-carboxylate Starting Material.

A solution of methyl 6-phthalimido-2,2-dimethylpenam-3-carboxylate-1-oxide (2.25 g., 6 mmol) and thionyl chloride (0.47 ml., 6.5 mmol) in 90 ml. dry carbon tetrachloride was refluxed for 1 hour, cooled and evaporated in vacuo to dryness. An nmr spectrum of the crude product showed a 2:3:3 mixture of methyl 7-phthalimido-3α-methyl-3β-hydroxycepham-4-carboxylate, methyl 6-phthalimido-2β-chloromethylpenam-2α-methyl-3-carboxylate, and methyl 6-phthalimido-2α-chloromethylpenam-2β-methyl-3-carboxylate, respectively. The products were separated by chromatography on silica gel and fully characterized by spectroscopy.

EXAMPLE II

To a refluxing solution of 3.76 g. (10 mmol) of methyl 7-phthalimido-3α-methyl-3β-hydroxycepham-4-carboxylate and 1.3 ml. (18 mmol) of thionyl chloride in 180 ml. of dry $CCl_4$, 1.67 ml. (11 mmol) of triethylamine in 20 ml. of dry $CCl_4$ was added dropwise over a 45 minute period. After addition of the triethylamine was completed, the mixture was refluxed for an additional 30 minutes. The solution was then filtered and evaporated in vacuo to dryness.

An nmr of the crude product showed it to contain, as a major product, methyl 6-phthalimido-2β-chloromethylpenam-2α-methyl-3-carboxylate, and, as minor products, methyl 6-phthalimido-2α-chloromethylpenam-2β-methyl-3-carboxylate and methyl 7-phthalimido-3-methyl-3-cephem-4-carboxylate. The crude product was taken up in 80 ml. of ethyl acetate and washed with water (2 × 60 ml.), brine (60 ml.), and dried over $MgSO_4$. Evaporation of the solvent gave a light yellow amorphous solid which was triturated with 50 ml. of a mixture of diethyl ether and ethyl acetate (1:1). The solid was filtered and washed with diethyl ether to give 1.72 g. of a white amorphous solid identified by nmr as methyl 6-phthalimido 2β-chloromethylpenam-2α-methyl-3-carboxylate. Evaporation of the filtrate from above gave a light yellow foam which was chromatographed on 50 g. of silica gel washed with acid. Eluting the column with 5:95 ethyl acetate:benzene gave an additional 740 mg. of the 2β-chloromethylpenam compound (62 percent total yield). Continued elution gave 350 mg. of a 1:1 mixture by nmr of the 2β-chloromethylpenam and methyl 6-phthalimido-2α-chloromethylpenam-2β-methyl-3-carboxylate. From the latter fraction was obtained 130 mg. of the 2α-chloromethylpenam compound.

EXAMPLE III

A solution of methyl 7-phthalimido-3α-methyl-3β-hydroxycepham-4-carboxylate (188 mg., 0.5 mmol), thionyl chloride (.08 ml., 1.1 mmol) and triethylamine (.14 ml., 1 mmol) in 20 ml. of dry carbon tetrachloride was refluxed for 70 minutes, cooled, filtered, and evaporated to dryness in vacuo. An nmr of the crude product showed it to be chiefly a 3:2 mixture of methyl 7-phthalimido-3-methyl-3-cephem-4-carboxylate and methyl 6-phthalimido-2β-chloromethylpenam-2α-methyl-3-carboxylate, respectively. Trace amounts of methyl 6-phthalimido-2α-chloromethylpenam-2β-methyl-3-carboxylate were also detected. The mixture was separated by chromatography over a silica gel column.

EXAMPLE IV

Preparation of p-Nitrobenzyl 7-Phthalimido-3α-methyl-3β-hydroxycepham-4-carboxylate Starting Material.

A mixture of N,N-dimethylacetamide (240 ml.), benzene (360 CH ml.) and concentrated sulfuric acid was dried azeotropically for ½ hour, p-Nitrobenzyl 6-phthalimido-2,2-dimethylpenam-3-carboxylate-1-oxide (20 g.) was added and the mixture refluxed for 7 hours using a Dean-Stark trap. After cooling, the reaction mixture was evaporated in vacuo to near dryness. The residue was then dissolved in 450 ml. of ethyl acetate and washed with water (2 × 300 ml.) and brine (200 ml.). The organic layer was dried over $MgSO_4$ and evaporated to dryness. Recrystallization of the residue from chloroform/cyclohexane gave 4.7 g. (39 percent) of p-nitrobenzyl 7-phthalimido-3α-methyl-3β-hydroxycepham-4-carboxylate as tan needles (mp 250°–251°): nmr (DMSO-$d_6$/$CDCl_3$) 77 (3, s, 3-$CH_3$), 200 (3, broad m, 3-OH + 2-$CH_2$), 271 (1, s, H), 322 (1, d, J=4 Hz, β-lactam H), 325 (2, s, ester $CH_2$), 347 (1, d, J=4 HZ, β-lactam H), 478 (8, m, ArH); ir (mull) 1790 (s) (β-lactam C=O), 1743 and 1782 (phthalimido C=O) and 1728 cm$^{-1}$ (ester C=O).

Anal. Calcd for $C_{23}H_{19}N_3O_8S$: C, 55,53; H, 3.85; N, 8.45; S, 6.45. Found: C, 55.26; H, 3.79; N, 8.15; S, 6.50.

EXAMPLE V

Triethylamine (1.2 ml., 8.8 mmol) in 20 ml. of 1,2-dichloroethane was added dropwise to a refluxing solution of p-nitrpbenzyl 7-phthalimido-3α-methyl-3β-hydroxycepham-4-carboxylate (3.98 g., 8 mmol) and thionyl chloride (0.7 ml., 9 mmol) in 250 ml. of 1,2-dichloroethane. After 1 hour at reflux, another 0.5 ml. thionyl chloride and 0.5 ml. triethylamine were added to the reaction mixture. After 2 more hours at reflux the dark brown mixture was cooled. Analysis of the dark brown mixture by nmr showed it to contain p-nitrobenzyl 6-phthalimido-2β-chloromethylpenam-2α-methyl-3-carboxylate and as minor products, p-nitrobenzyl 6-phthalimido-2α-chloromethylpenam-2β-methyl-3-carboxylate and p-nitrobenzyl 7-phthalimido-3-methyl-3-cephem-4-carboxylate. The mixture was evaporated in vacuo to dryness. The crude product was then taken up in 80 ml. chloroform, refluxed with 7 g. of decolorizing carbon and filtered. The filtrate was washed with water (2× 50 ml.) and brine (50 ml.), dried and evaporated in vacuo to dryness. Recrystallization from ethyl acetate/diethyl ether/pet. ether gave 2.3 g. (56 percent) of p-nitrobenzyl 6-phthalimido-2β-chloromethylpenam-2α-methyl-3-carboxylate as tan needles (mp 161°–163°): nmr ($CDCl_3$) 93 (3, s, 3$CH_3$), 220 and 270 (2, ABq, J=12 HZ), 311 (1, s, 4-H), 319 (2, s, ester $CH_2$), 343 (2, s, β-lactam protons), and 478 Hz (8, m, ArH): ir ($CHCl_3$) 1809 (β-lactam C=O), 1735 (ester C=O), 1743 (s) and 1787 cm$^{-1}$ (phthalimido C=O).

Anal. Calcd for $C_{23}H_{18}N_3ClO_7S$: C, 53.53; H, 3.52; N, 8.14; Cl, 6.87. Found: C, 53.70; H, 3.65; N, 8.33; Cl, 6.90.

EXAMPLE VI

Preparation of p-Methoxybenzyl 7-Phthalimido-3α-methyl-3β-hydroxycepham-4-carboxylate Starting Material.

A mixture of 4 drops of conc, sulfuric acid in 60 ml. N,N-dimethylacetamide and 80 ml. of benzene was dried azeotropically for 30 minutes. p-Methoxybenzyl 6-phthalimido-2,2-dimethylpenam-3-carboxylate-1-oxide (5.0 g., 10 mmol) was then added. The reaction mixture was refluxed for 30 minutes, cooled and evaporated to near dryness. Ethyl acetate (150 ml.) was added to the product, and the resulting solution was evaporated in vacuo to dryness. A crystalline product formed during evaporation of the solvent. The product was then slurried with 50 ml. of ethyl acetate. Filtration gave 3.1 grams (62 percent) of p-methoxybenzyl 7-phthalimido-3α-methyl-3β-hydroxycepham-4-carboxylate as colorless crystals, mp 216°–217°: nmr (CDCl$_3$) 76 (3, s, 3-CH$_3$), 149 and 205 (2, ABq, J=14 Hz, 2-CH$_2$), 230 (3, s, OCH$_3$), 274 (1, s, 4-H), 300 (1, broad s, OH), 309 (2, s, ester CH$_2$), 324 (1, d, J=4.5 Hz, azetidinone H), 335 (1, d, J=4.5 Hz, azetidinone H), 426 (4, q, p-CH$_3$OC$_6$H$_4$ArH) and 469 Hz (4, m, phthalimido H); ir (mull) 3460 (OH), 1725 (ester C=O), 1739 and 1781 (phthalimido C=O) and 1802 cm$^{-1}$ (azetidinone C=O, shoulder).

Anal. Calcd for C$_{24}$H$_{22}$N$_2$O$_7$S: C, 59.74; H, 4.60; N, 5.81; O, 23.21; S, 6.65. Found: C, 59.47; H, 4.50; N, 5.73; O, 23.41; S, 6.90.

EXAMPLE VII

Triethylamine (2.10 ml., 15 mmol), in 50 ml. 1,2-dichloroethane was added dropwise to a refluxing solution of p-methoxybenzyl 7-phthalimido-3α-methyl-3β-hydroxycepham-4-carboxylate (7.23 g., 15 mmol) and thionyl chloride (1.30 ml., 16 mmol) in 400 ml. of 1,2-dichloroethane After 90 minutes at reflux another 0.3 ml. of thionyl chloride and 0.2 ml. of triethylamine were added to the reaction mixture. The mixture was then refluxed for an additional 30 minutes and cooled. The crude reaction mixture contained p-methoxybenzyl 6-phthalimido-2 -chloromethylpenam-2 -methyl-3-carboxylate and p-methoxybenzyl 7-phthalimido-3-methyl-3-cephem-4carboxylate as minor products and p-methoxybenzyl 6-phthalimido-2β-chloromethylpenam-2α-methyl-3-carboxylate as the major product. The mixture was evaporated to dryness. The crude product was chromatographed on a silica gel column (250 g., 4 × 35 cm.) which was developed with 6 percent benzene in ethyl acetate taking 22 ml. fractions every 15 minutes. A total of 4.5 grams (60 percent) of p-methoxybenzyl 6-phthalimido-2β-chloromethylpenam-2α-methyl-3-carboxylate was obtained: nmr (CDCl$_3$) 90 (3, s, 3-CH$_3$), 229 (3, s, OCH$_3$). 219 and 267 (s, ABq, J=12 Hz, 2-CH$_2$), 306 (1, s, 4-H), 310 (2, s, ester CH$_2$) 343 (2, s, azetidinone protons), 426 (4, q, benzyl ArH), and 469 Hz (4, m, phthalimido H): ir (CHCl$_3$) 1806 (azetidinone C=O), 1736 (ester C=O), and 1745, 1788 cm$^{-1}$ (phthalimido C=O).

Anal. Calcd for C$_{24}$H$_{21}$N$_2$ClO$_6$S: C, 57.54; H, 4.23; N, 5.59; S, 6.40; Cl, 7.08. 4 Found: C, 57.35; H, 4.42; N, 5.42; S, 6.19; Cl, 7.79.

EXAMPLE VIII

A solution of methyl 7-phthalimido-3α-methyl-3β-hydroxycepham-4-carboxylate (374 mg., 1 mmol) and phosphorus pentachloride (315 mg., 1.5 mmol) in 25 ml. of dry carbon tetrachloride was refluxed for 45 minutes. Triethylamine (0.14 ml., 1 mmol) was then added to the reaction mixture. After refluxing for an additional 45 minutes, the mixture was cooled, filtered, and the filtrate was evaporated to dryness. An nmr spectrum of the crude product showed approximately a 5:5:1 mixture of methyl 7-phthalimido-3-methyl-3-cephem-4-carboxylate, methyl 6-phthalimido-2β-chloromethylpenam-2α-methyl-3-carboxylate, and methyl 6-phthalimido-2α-chloromethylpenam-2β-methyl-3-carboxylate, respectively.

EXAMPLE IX

Methyl 6-phthalimido-2α-methyl-2β-chloromethylpenam-3-carboxylate (1.44 g.; 3.65 mmole) was chromatographed on a 4 × 70 cm. column packed with 80 g. (15 cm.) of acid washed silica gel. The 2β-chloromethylpenam compound was washed onto the column with 100 ml. (out of a total of 200 ml.) of toluene at an initial rate of 1.8 ml. per minute. The flow rate was then shut off, and the column was allowed to stand for 2.5 days. The column was then developed at 1.0 ml. per minute using a mixture containing 10 percent ethyl acetate in toluene. Fractions of 20 ml. each were collected. Fractions 41–80 gave 0.57 g. of methyl 7-phthalimido-3α-methyl-3β-chlorocepham-4-carboxylate: nmr (CDCl$_3$) 105 (s, 3, C$_3$-αCH$_3$); 184,206 (ABq, 2, C$_2$-H); 297 (s, 1, C$_4$-H); 324 (d, 1, C$_6$-H): and 337 Hz (d, 1, C$_7$-H).

We claim:
1. Process for converting a 3-methyl-3-hydroxycepham compound, which comprises the step of reacting a compound of the formula

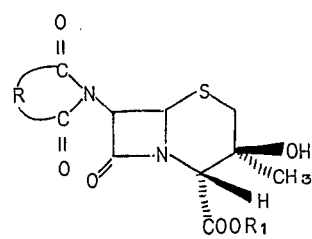

with a halogen reagent selected from the group consisting of PX$_5$ and SOX$_2$ in the presence of at least about one mole of an alkaline reagent selected from the group consisting of a tertiary amine and an inorganic alkaline salt per each mole of the 3-methyl-3-hydroxycepham compound and at a temperature within the range of from about 60°C. to about 150°C. to obtain a mixture of a compound of the formula IV

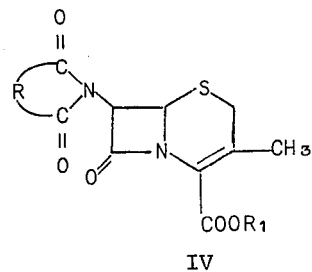

IV a compound of the formula V

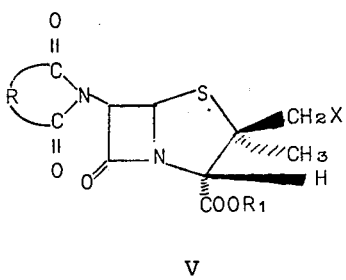

V and a compound of the formula VI

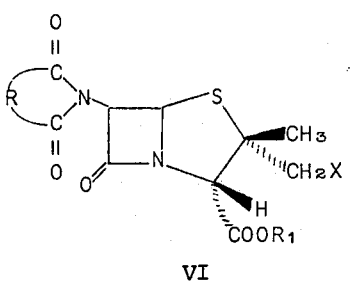

VI in which, in the above formulae, R is the residue of an imide derived from a dicarboxylic acid, $R_1$ is a carboxy protecting group and X is chlorine or bromine.

2. Process of claim 1, in which R is $C_2$-$C_4$ alkylene, $C_2$-$C_4$ alkenylene, -$CH_2$-Y-$CH_2$- in which Y is oxygen or sulfur, 1,2-cyclohexylene, 1,2-phenylene, 1,2-cyclohexenylene, or a substituted derivative of any of the above having from 1 to 4 substituents selected from the group consisting of $C_1$-$C_3$ alkyl, $C_1$-$C_3$ alkoxy, nitro, fluoro, chloro, bromo, or iodo.

3. Process of claim 2, in which R is $C_2$-$C_4$ alkylene, $C_2$-$C_4$ alkenylene, -$CH_2$-Y-$CH_2$- in which Y is oxygen or sulfur, 1,2-cyclohexylene, 1,2-phenylene, or 1,2-cyclohexenylene.

4. Process of claim 3, in which $R_1$ is $C_1$-$C_4$ alkyl, 2,2,2-trihaloethyl, 2-iodoethyl, benzyl, p-nitrobenzyl, succinimidomethyl, phthalimidomethyl, p-methoxybenzyl, benzhydryl, $C_2$-$C_6$ alkanoyloxymethyl, phenacyl, or p-halophenacyl.

5. Process of claim 4, in which the halogen reagent is present in an amount of from about 1.1 to about 2.0 moles per each mole of the 3-methyl-3-hydroxycepham compound.

6. Process of claim 5, in which the alkaline reagent is a tertiary amine.

7. Process of claim 6, in which the tertiary amine is present in an amount of from about 1.0 to about 2.0 moles per each mole of the 3-methyl-3-hydroxycepham compound.

8. Process of claim 7, in which X is chlorine.

9. Process of claim 8, in which the halogen reagent is phosphorous pentachloride.

10. Process of claim 8, in which the halogen reagent is thionyl chloride.

11. Process of claim 8, in which the tertiary amine is triethylamine.

12. Process of claim 11, in which R is 1,2-phenylene.

13. Process of claim 12, in which $R_1$ is p-nitrobenzyl.

14. Process of claim 12, in which $R_1$ is p-methoxybenzyl.

* * * * *